United States Patent [19]

Michaels et al.

[11] Patent Number: 5,917,135
[45] Date of Patent: Jun. 29, 1999

[54] GAS CONCENTRATION SENSOR AND CONTROL FOR OXYGEN CONCENTRATOR UTILIZING GAS CONCENTRATION SENSOR

[75] Inventors: Gregory A. Michaels, Seven Hills; Homayoun Birangi, Willoughby, both of Ohio

[73] Assignee: Invacare Corporation, Elyria, Ohio

[21] Appl. No.: 08/873,645

[22] Filed: Jun. 12, 1997

Related U.S. Application Data

[60] Provisional application No. 60/020,481, Jun. 14, 1996, and provisional application No. 60/019,753, Jun. 14, 1996.

[51] Int. Cl.$^6$ .................................................. B01D 53/053
[52] U.S. Cl. .................. 95/11; 95/12; 95/21; 95/101; 95/130; 96/111; 96/112; 96/130; 96/144
[58] Field of Search ............................. 95/8, 11, 12, 19, 95/21, 96–105, 130; 96/111–117, 130, 143, 144

[56] References Cited

U.S. PATENT DOCUMENTS

| | | | |
|---|---|---|---|
| 2,944,627 | 7/1960 | Skarstrom | 95/26 |
| 3,142,547 | 7/1964 | Marsh et al. | 95/100 |
| 3,280,536 | 10/1966 | Berlin | 95/105 |
| 3,313,091 | 4/1967 | Berlin | 95/105 |
| 3,392,574 | 7/1968 | Lemon et al. | 73/53 |
| 3,922,149 | 11/1975 | Ruder et al. | 95/130 X |
| 4,197,095 | 4/1980 | White, Jr. et al. | 96/113 X |
| 4,247,311 | 1/1981 | Seibert et al. | 96/111 |
| 4,259,548 | 3/1981 | Fahey et al. | 179/5 R |
| 4,331,455 | 5/1982 | Sato | 95/122 X |
| 4,331,457 | 5/1982 | Mörner | 96/116 |
| 4,336,590 | 6/1982 | Jacq et al. | 364/418 |
| 4,349,357 | 9/1982 | Russell | 96/117 X |
| 4,449,990 | 5/1984 | Tedford, Jr. | 95/26 |
| 4,459,266 | 7/1984 | Lamoreaux | 422/86 |
| 4,472,177 | 9/1984 | Sircar | 95/98 X |
| 4,516,424 | 5/1985 | Rowland | 73/23 |
| 4,545,790 | 10/1985 | Miller et al. | 96/117 |
| 4,561,287 | 12/1985 | Rowland | 73/23 |
| 4,627,860 | 12/1986 | Rowland | 96/111 |
| 4,643,743 | 2/1987 | Grader | 95/130 X |
| 4,684,377 | 8/1987 | Haruna et al. | 95/130 X |
| 4,698,075 | 10/1987 | Dechene | 96/116 |
| 5,002,591 | 3/1991 | Stanford | 96/115 X |
| 5,071,453 | 12/1991 | Hradek et al. | 95/8 X |
| 5,104,426 | 4/1992 | Yamada et al. | 95/11 |
| 5,247,826 | 9/1993 | Frola et al. | 73/24.01 |
| 5,340,381 | 8/1994 | Vorih | 96/130 X |
| 5,469,372 | 11/1995 | McBrearty et al. | 364/550 |
| 5,486,226 | 1/1996 | Ross et al. | 96/144 X |
| 5,529,607 | 6/1996 | Tan | 95/130 X |
| 5,627,323 | 5/1997 | Stern | 73/861.28 |

FOREIGN PATENT DOCUMENTS

| | | |
|---|---|---|
| 0 250 235 A1 | 6/1986 | European Pat. Off. . |
| 38 35 164 A1 | 4/1989 | Germany . |
| 296 05 889 U1 | 8/1989 | Germany . |
| WO 87/02770 | 5/1987 | WIPO . |

*Primary Examiner*—Robert Spitzer
*Attorney, Agent, or Firm*—Hudak & Shunk Co., L.P.A.

[57] ABSTRACT

An acoustic oxygen sensor is provided which can be used in the output lines leading from the sieve beds. This sensor can be used in communication with a microprocessor to control the production and evacuation cycles of the sieve beds, i.e., for example to determine the period for which a bed is supplied with compressed air and communicates with the reservoir as well as to determine the pressure of the compressed air and to determine the amount of time that the product gas is fed through the flow equalization path to supply an aliquot of purging gas to a used bed. In the feedback loop, the microprocessor utilizes the measured oxygen concentration and flow rate to optimize the settings necessary to achieve maximum oxygen concentration and flow rate efficiency. Since the microprocessor has the ability to make incremental changes and compare relative values, the optimum values can be determined empirically eliminating the need to perform complex theoretical calculations.

26 Claims, 4 Drawing Sheets

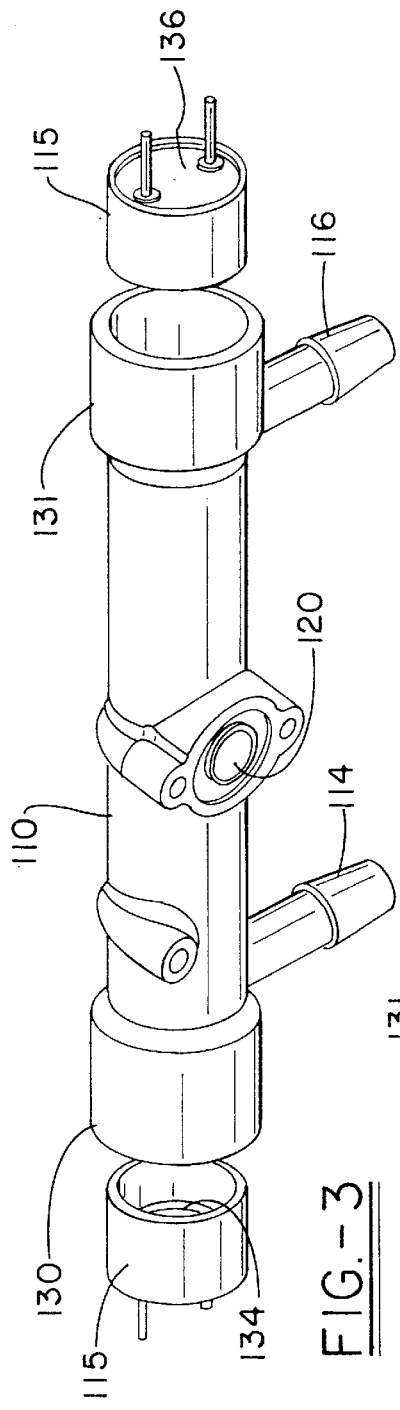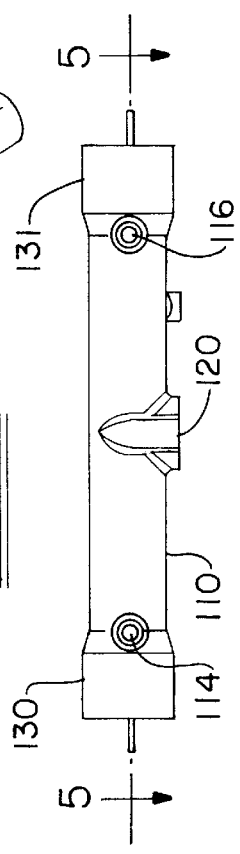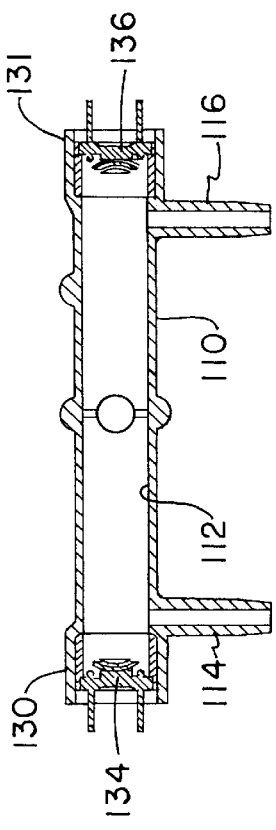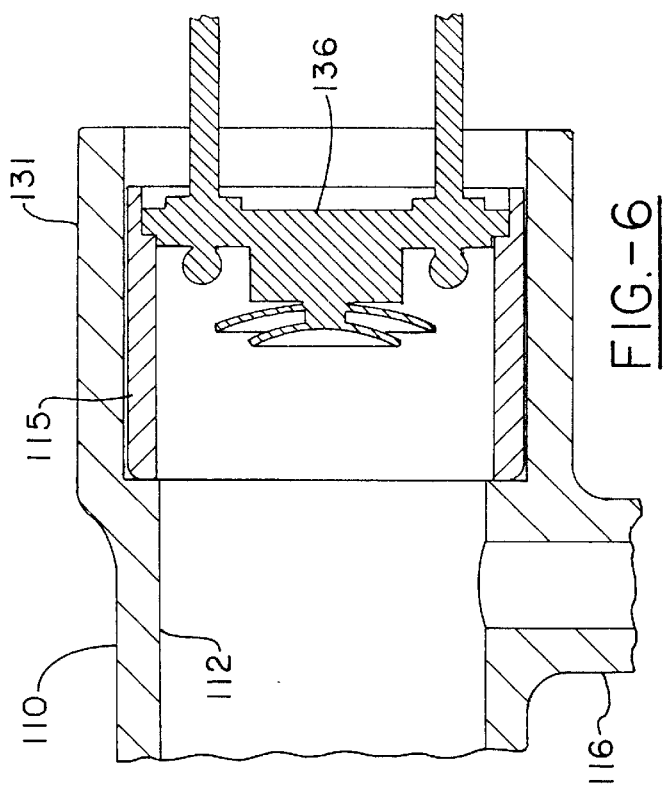

GAS CONCENTRATION SENSOR AND CONTROL FOR OXYGEN CONCENTRATOR UTILIZING GAS CONCENTRATION SENSOR

CROSS-REFERENCE

The present application claims priority to U.S. Provisional patent application Ser. No. 60/020,481, filed Jun. 14, 1996, entitled "Acoustic Sensor for Controlling Sieve Bed Operation," and further claims priority to U.S. Provisional patent application Ser. No. 60/019,753, filed Jun. 14, 1996, entitled "Acoustic Sensor."

FIELD OF INVENTION

The present invention relates to fractionating gases and more specifically to a control system utilizing an acoustic sensor for regulating the flow parameters of molecular sieve beds in an oxygen concentrator. In a separate embodiment, the invention relates to a specific acoustic sensor which can be used, inter alia, for oxygen concentrators.

BACKGROUND OF THE INVENTION

Various applications exist for the separation of gaseous mixtures, and in particular for the separation of nitrogen from atmospheric air to provide a source of highly concentrated oxygen. These applications include the provision of elevated concentrations of oxygen for patients requiring the same in their breathing air and for flight personnel. Additional applications relate to processes such as drying high-purity gases such as separating hydrogen from hydrocarbons.

U.S. Pat. No. 2,944,627, issued Jul. 12, 1960, to Charles Skarstrom illustrates an early apparatus and method for fractionating gases having first and second fractionating vessels packed with molecular sieve material which selectively adsorbed one or more components of the gas so as to pass through an enriched product gas. A cross-over valving assembly allowed for a flow correspondence between the vessels and with a waste gas discharge. Product gas from a vessel was channelled to a primary product outlet with a large fraction being channeled to the other vessel. This fraction flushed the adsorbed or waste gases which had been trapped by the other vessel. The cross-over valve assembly cyclically switched the connection of the vessels with the incoming gas and the waste gas discharge. This cyclic switching of the vessels provided a regular flow of the primary product gas from the primary product outlet.

U.S. Pat. No. 3,313,091, to Berlin, improved upon the Skarstrom system through the utilization of a vacuum pump to draw adsorbed or waste gases from the vessel or bed being purged. Additionally this invention utilized a more complex valving system to produce a cycle which included vessel or bed pressure equalization, repressurization product production, bed pressure equalization, dumping, and purging.

U.S. Pat. No. 4,222,750, to Gauthier et al. related to a specifically defined timing cycle in which primary product gas from the adsorbing bed was passed through the desorbing bed during the desorption cycle. The vessels were connected to a compressor during a period of adsorption and to a vacuum pump during a period of desorption.

U.S. Pat. No. 4,449,990, to Tedford Jr. improved upon these prior art patents by teaching a method and apparatus for fractionating oxygen in which a pair of molecular sieve beds were cyclically connected in a timed cycle by a first cross-over valve (i.e., a four-way valve) with a source of pressurized air and a method of depressurizing the bed. The outlet ends of the beds were further connected by a flow path referred to as a pressure equalization flow path including a pressure equalization valve ("PE" valve) for selectively opening and closing the flow path. The path included two flow conduits including a limited conduit which is always open and a regulated flow conduit which has the PE valve for variable flow rate. Further in that patent, a timing and control circuit regulated the cross-over valve such that the pressure equalization valve was open 1 percent of the cycle duration before the cross-over valve reversed positions and was closed 2 percent of the cycle duration after the cross-over valve changed positions.

Generally in the prior art as represented by these and other patents, an equalization valve is disposed between a pair of check valves at the outlet ends of a pair of sieve beds in an oxygen concentrator system. While the equalization valve was referred to by Tedford as a pressure equalization valve (i.e., a "PE" valve), in this invention we will refer to the corresponding valve as a concentration equalization valve (i.e., a "CE" valve). Ultimately the same result is achieved of allowing a purge supply of product gas to enter a used bed; however, with a pressure-based supply, the rationale for using the valve varies slightly. Specifically the equalization valve acts to dampen the oscillation of the output gas concentration into the product tank which may otherwise occur. An oxygen concentration sensor located in a bleed line from the product tank measures and provides an indication of whether or not a certain oxygen level is met. For example, normal or acceptable operation may exhibit a green light at a reading of 85 percent or above; a yellow light may be illuminated at a reading between 73 and 85 percent; and a red light illuminates at a reading below 73 percent and the device subsequently powers down. This information is merely displayed to the patient or technician. That is, the technician manually controls the equalization valve in an effort to fine-tune the oxygen supply to the patient based on the indicator lights and oxygen readings.

In accordance with the present invention, the oxygen sensor communicates with the concentration equalization valve by means of the microprocessor which utilizes a closed-loop control to provide automated operation and optimization of oxygen levels from the sieve beds to the patient. In the prior art as represented by the '990 patent, the equalization valve is set manually. This valve provides for the cyclic flow of gas from the producing bed to the evacuated bed to provide sieve bed purge and to stabilize the oxygen content of the product gas passed into the product reservoir. Specifically, the valve settings change the time that the valve is open in one direction allowing purge gas (i.e., from one bed to the second) as compared to the time that the valve is open allowing flow in the second direction.

In the present invention, a closed-loop control circuit is provided to continuously and automatically regulate the performance of the cross-over valve, of the concentration equalization valve and the compressor. An acoustic oxygen sensor located between the check valves at the output ends of the fractionation beds communicates information to the microprocessor which is programmed to evaluate the oxygen output of the sieve bed and thereby used to control operation of the production cycle (i.e., fill, purge, evacuate).

Further in accordance with this invention, the operation of the oxygen concentrator is optimized through the direct use of information regarding the oxygen output of the sieve beds. This information can be used to trigger the pressure swing adsorption cycle. This cycle can be initiated by a sensed drop in oxygen concentration with the opening of the concentration equalization valve (or alternatively with the switching of the cross-over valve). The cross-over valve can be timed to switch thereafter. The concentration equalization valve allows oxygen from the first sieve bed to mix with oxygen from the second sieve bed. The amount of time that gas is allowed to flow into the used sieve bed is determined by the concentration equalization valve adjustment. Closed-loop feedback based on acoustically derived oxygen concentration provides the optimum cycling for the pressure swing adsorption cycle (i.e., the cycle) and for the cross-over between the pressurization and depressurization means. Optimization may change as a result of compressor age, the filter condition, and line voltage. By using an acoustic oxygen sensor to measure output, the pressure swing cycle can be directly controlled using electronic control means such as an integrated or remote microprocessor programmed with the appropriate software.

U.S. Pat. No. 5,247,826, to Frola et al., relates to an acoustic gas concentration sensor used in an oxygen concentrator wherein two piezoelectric transducers are interconnected by an elongated coiled tube which provides a flow path for the gas. Periodically and alternatively, one of the transducers is energized with a single, short burst of energy or pulse to transmit a sonic wave through the gas to the other transducer. The travel time for the sonic wave is measured and used to calculate the oxygen concentration.

U.S. Pat. No. 5,627,323, to Stern, similarly relates to an ultrasonic binary gas measuring device in which a single ultrasonic wave travels between two piezoelectric transducers and the time of travel of the wave back and forth through a flow chamber is measured and used by the microprocessor to calculate the gas concentration and/or the standard flow rate for the gas.

The present invention additionally relates to an acoustic oxygen sensor which uses a pulse (or pulsed transmission) rather than a continuous sound wave in one of two manners for monitoring the oxygen content. For example, a transmitter at one end of a predetermined path sends a pulse toward a receiver disposed at the other end. A particular cell length and period of pulse time, e.g., one second, is selected. A pulse is transmitted from one end of the cell and detected at the other end. The receiver then counts the pulses and provides a signal back to the transmitter to send another pulse upon detection of the first pulse. The cumulative number of pulses over the fixed period of time provides an alternative solution to the extended path length used in the prior art. The path length in essence is substantially increased without actually increasing the cell length. Close tolerances are not required for the cell length, i.e., the distance between the transducers, so long as the cell is calibrated using a known gas at a known temperature passed through the cell.

The change in the number of pulses is proportional to the changes in the ambient conditions. Since the time between comparative pulse transmission periods is short (i.e., around a second), it is assumed that variables such as oxygen concentration and temperature are relatively static during that period. Therefore, by positioning a pair of transducers a fixed distance apart, sending a pulse from the transmitter to the receiver, or even back again, over a fixed interval of time, the difference in number of pulses counted is therefore related to the change in the oxygen concentration.

While the present oxygen sensor is not as fast in responding as are the prior art sensors (i.e., this oxygen sensor waits an entire transmission period before calculating a value), the present sensor has the advantage of providing an easier measurement, i.e., rather than measuring extremely small increments of time, the sensor counts a substantial number of pulses sent over a larger increment of time. This represents a more cost-efficient device and also provides for a more stable calculated value. Additionally, the current invention provides a temperature sensor which is exposed to the flow path but does not project into the path so as to influence the projected calculation.

SUMMARY OF THE INVENTION

An oxygen concentrator is provided having first and second molecular sieve beds for the fractionation of oxygen from air. The sieve beds are connected by means of a cross-over valve, i.e., a four-way valve, to a compressor or alternatively are vented to atmosphere for evacuation of a used bed. The beds are used cyclically so that one bed is receiving pressurized air from the compressor while the other bed receives purified product gas and/or is vented to atmosphere for evacuation. A concentration equalization flow path having a concentration equalization valve is connected to the output end of the first and second sieve beds. Additionally, the output ends of the sieve beds are connected to a product tank which supplies purified oxygen to the patient. Product gas flow from the output ends of the sieve beds through check valves to the product tank.

In accordance with one aspect of the invention, acoustic oxygen sensors can be used in the output lines, for example between the check valves, leading from the sieve beds. These sensors can be used in communication with a microprocessor to control the production and evacuation cycles of the sieve beds, i.e., for example to determine the period for which a bed is supplied with compressed air and communicates with the reservoir as well as to determine the pressure of the compressed air and to determine the amount of time that the product gas is fed through the flow equalization path to supply an aliquot of purging gas to a used bed. In the feedback loop, the microprocessor utilizes the measured oxygen concentration to optimize the settings such as the cross-over valve and the concentration equalization valve, necessary to achieve maximum oxygen concentration and flow rate efficiency. Since the microprocessor has the ability to make incremental changes and compare relative values, the optimum values can be determined empirically eliminating the need to perform complex theoretical calculations.

In accordance with a second aspect of the invention, an acoustic oxygen sensor is provided which can be used in the first embodiment of the invention or alternatively in a removable testing device used, for example, to evaluate the oxygen concentration and flow rate delivered. The oxygen sensor comprises a flow tube which provides a relatively smooth and unobstructed flow path including a recessed portion for non-laminar fluid communication with a thermocouple or other temperature-sensing means. The oxygen sensor has first and second transmitting receiver means at either ends of the flow path such as, for example, piezoelectric transducers. A first transducer will transmit a pulsed signal to the second transducer. When the pulsed signal is received by the second transducers, the first transducer emits a second pulse. The sending and receiving of pulsed signals thus continues for a defined period and a cumulative number of pulsed receptions are calculated. The process is reversed so that the second transducer transmits to the first transducer which is subsequently used as a receiver. The difference in pulsed transmissions is determined. This value is used assuming a constant oxygen concentration and temperature for the pulse periods. This enables a determination of flow rate.

In accordance with the present invention, there is provided a method of and control apparatus for a device which fractionates components of a gaseous mixture. Concurrently, the gaseous mixture is supplied under pressure to a bed of a physical separation medium which adsorbs at least one adsorbable component and passes at least one substantially nonadsorbable component of the mixture while a second bed is being evacuated. Before reaching the capacity of the gaseous mixture-supplied bed to adsorb the adsorbable component, the beds are brought toward pressure equilibrium by allowing the gas to flow between the beds. While gas is flowing between the beds, the supply of the gaseous mixture to and the evacuation of the beds are reversed. That is, the gaseous mixture is supplied to the heretofore evacuated bed and the heretofore gaseous mixture-supplied bed is evacuated. Thus, the control means allows for alternate selective pressurization of the beds (i.e., a pressure swing adsorption cycle), meaning that cyclically one bed and then the other is connected through a concentration equalization flow path with a cross-over valve to an air compressor. Subsequent to reversing the supply of the gaseous mixture and the evacuation of the beds, the concentration equalization flow is terminated. These steps are cyclically repeated to provide continuing production of the nonadsorbable component. The invention encompasses a novel method and device for controlling the pressure equilibrium between the first and second sieve beds and/or the oxygen concentration flow rate to a patient. This new control method achieves a higher efficiency and further facilitates remote control of the oxygen concentrator.

In accordance with another aspect of the present invention, there is also provided an apparatus for physically separating molecules of oxygen from a gaseous mixture. The apparatus comprises first and second beds each containing a physical separation material. A cross-over valving means selectively connects an inlet of one of the first and second beds with a supply of the gaseous mixture under pressure and vents the inlet end of the other bed to atmosphere. A control means causes the cross-over valving means to connect each of the first and second beds cyclically with the gaseous mixture supply, i.e., compressor, and to be vented for evacuation to atmosphere. The period of time in which one of the beds goes through a cycle of being connected with the gaseous mixture supply and the vacuum pump is denoted as a cycle duration. In a timing cycle-based system, a cycle duration may be a constant amount of time. Alternatively, it is possible to regulate the production cycle based on the output pressure from the beds as measured by pressure transducers in the outlet flow path. In this instance, the cycle duration will be determined by pressure changes and may be a variable-time period. However, in accordance with the present invention, the cycle duration may be defined directly by the oxygen concentration. A flow path which connects outlets of the first and second beds has a gas flow capacity which is sufficient to bring the first and second beds substantially into pressure equilibrium. A concentration equalization valve which selectively permits and prevents gas flow through the flow path is in communication with the control means. The control means causes the concentration equalization valve to open for a portion of the cycle duration before each actuation of the cross-over valving means and to be closed for a portion of the cycle duration after each actuation of the cross-over valving means. A reservoir tank is operatively connected with the first and second bed outlets by unidirectional valving means to collect oxygen which has been separated by the first and second beds. The control means evaluates the relative flow setting (i.e., time to achieve equilibrium) between the two beds. This control means is signalled by the microprocessor in response to readings from the oxygen sensor.

An additional aspect of the invention relates to the use of a control system which utilizes a variable pressure-based control to drive the cross-over valve and switch the cycling relative to the first and second molecular sieve beds. Specifically, the control will readjust the sieve bed pressure in order that the residence time of the fractionation gases stay within a certain defined range. Thus, for example, if a given sieve bed size and packing arrangement requires a minimum diffusion time, the controller will readjust the pressure to compensate such as for a higher flow rate which a higher-power compressor might provide. Thus, the circuit applies logic utilizing pressure and time parameters to define the product cycle duration. Likewise, oxygen concentration at the bed output can be utilized to define the product cycle duration.

In an additional aspect of the invention, a new acoustic oxygen sensor is provided which can be used in the control system of this invention as well as for external monitoring functions. As an example of external monitoring functions, devices are available which monitor the oxygen concentration output at the patient supply line using prior art acoustic oxygen sensors. These sensors suffer from requiring a highly precise time measurement and lacking signal stability. In contrast, the acoustic oxygen sensor of the present invention is less sensitive but more stable as a result of a more robust design strategy.

A primary advantage of the present invention is that it provides relatively high primary product production capacity.

Another advantage of the present invention is that it produces oxygen at a sufficiently high flow rate and purity for medical applications and for providing oxygen-enriched breathing air for patients.

Another advantage of the present invention is that the control functions are delegated to an improved microprocessor to reduce the need for field servicing by a technician.

BRIEF DESCRIPTION OF THE DRAWINGS

FIG. 3 is a bottom view of the oxygen sensor of the present invention;

FIG. 4 is a side view of the oxygen sensor;

FIG. 5 is a cross-section taking along line 5—5 of FIG. 4;

FIG. 6 is an enlargement of the transmitter/receiver shown in FIG. 5;

DETAILED DESCRIPTION OF THE PREFERRED EMBODIMENT

Figure 1:
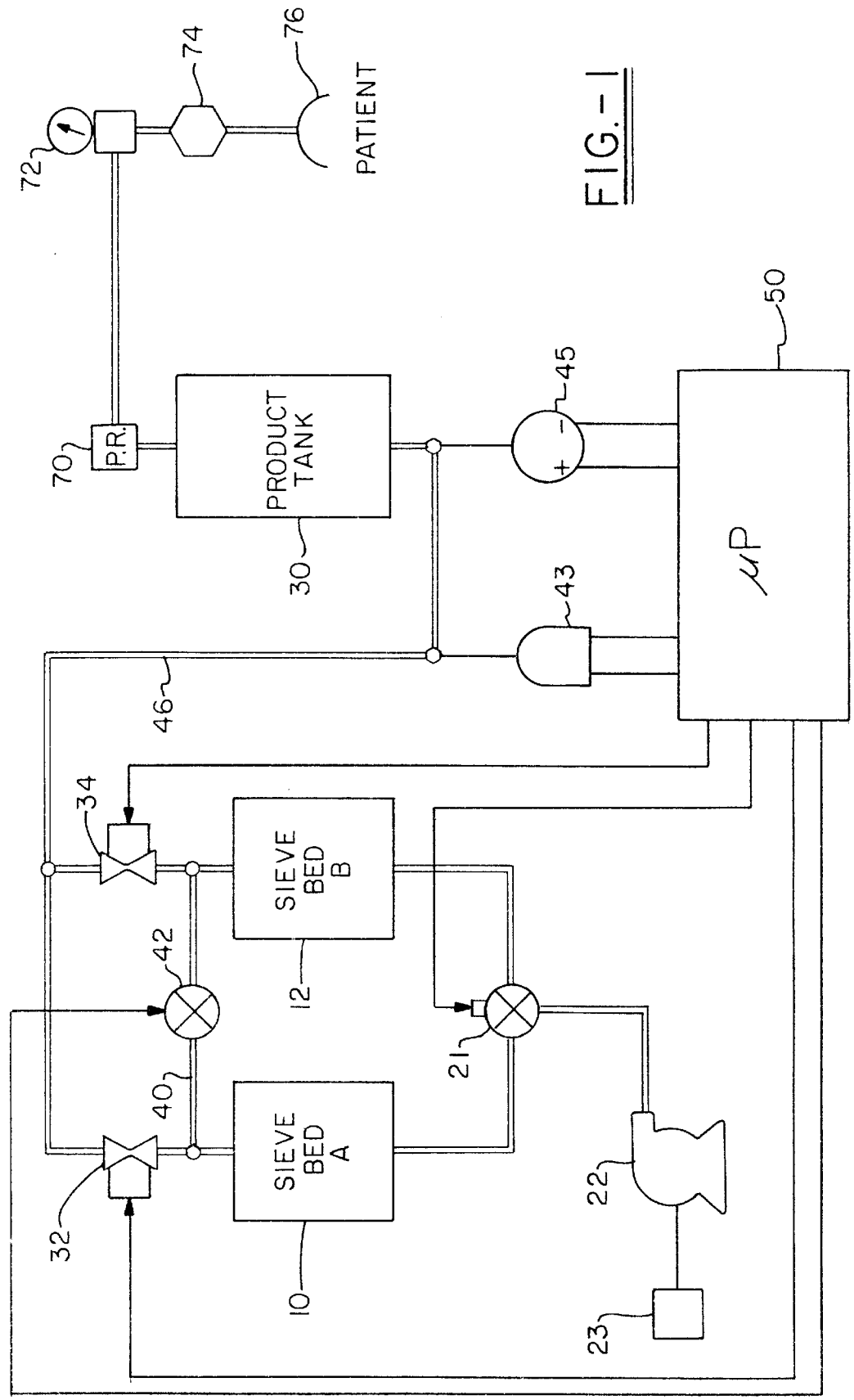
FIG. 1 is a block diagram of an apparatus in accordance with the present invention for separating a primary product gas from a gaseous mixture.

With reference to FIG. 1, the apparatus includes at least two beds 10 and 12 which are filled with a physical separation medium or material. The separation material selectively adsorbs one or more adsorbable components and passes one or more nonadsorbable components of such a gaseous mixture. The physical separation material is a molecular sieve with pores of uniform size and essentially the same molecular dimensions. These pores selectively adsorb molecules in accordance with molecular shape, polarity, degree of saturation, and the like. In the preferred embodiment, the physical separation medium is an aluminasilicate composition with 4 to 5 Å (Angstrom) pores. More specifically, the molecular sieve is a sodium or calcium form of aluminasilicate, such as type 5A zeolite. Alternately, the aluminasilicate may have a higher silicon-to-aluminum ratio, larger pores, and an affinity for polar molecules, e.g., type 13× zeolite. The zeolite adsorbs nitrogen, carbon monoxide, carbon dioxide, water vapor, and other significant components of air.

A cross-over valving means 21, which is preferably includes a four-way valve, selectively and cyclically connects the inlet end of two beds, one at a time, during a production phase with a source of the gas mixture, e.g., air under pressure supplied from a compressor 22, while the other bed is vented to atmosphere during a purge phase. Specific to the preferred embodiment, the cross-over valving means selectively connects one of the beds with an air pump or compressor 22 which supplies air under about 15–30 pounds per square inch. Of course, vacuum can also be used during the purge phase with the present invention to enhance evacuation. The compressor is connected to a drive motor 23, in the preferred embodiment about a ¼-horsepower electric motor. A solenoid (not shown) or other cross-over valve actuating means selectively causes the cross-over valving means to move alternately between first and second positions. In the first position, illustrated in FIG. 1, the first bed 10 is connected with the compressor 22 to cause nitrogen adsorption and oxygen enrichment in the product gas, and the second bed 12 is vented to atmosphere to allow evacuation. In the second position, the first bed is vented to atmosphere to allow evacuation and the second bed is connected with the air compressor to cause nitrogen adsorption.

As the gas mixture is introduced through a bed inlet to an adsorbed, gas-free or regenerated bed, an adsorption zone of finite, relatively large size is formed. This adsorption zone is a region of the bed in which the full capacity of the adsorbent to hold the adsorbable components has not been reached. The composition of the gas in the voids of the zeolite varies from substantially pure primary-product gas at the outlet end, to the ambient gaseous mixture composition at the inlet end. This adsorption zone moves from the bed inlet toward a bed outlet with a velocity significantly less than the superficial gas velocity in the bed. When the adsorption zone reaches the outlet end of the bed, adsorbable components begin to flow through the bed outlet into the nonadsorbable primary product stream. This time is hereinafter referred to as the "breakthrough." For a given gaseous composition, the breakthrough is defined by the size and configuration of the bed container as well as the packing configuration of the molecular sieve and the flow rate and bed gas pressure. The configuration is generally cylindrical, while the volume can vary from about 0 to 6 liters, and more specifically 3, 5, and 6 liters, respectively. The breakthrough is the time required for the diffusion reaction as the nitrogen saturates and is weakly bonded to the sieve bed. When breakthrough occurs, primary product-enriched bed gas in the zeolite voids varies from a higher primary product gas concentration at the bed outlet to a lower concentration at the bed inlet. In the preferred embodiment, the primary product-enriched bed gas is about 80 percent primary product at breakthrough. While adsorption is occurring in one bed, the adsorbable components adsorbed by the separation medium of the other bed are purged from the other bed because of the drop in pressure due to atmospheric venting and because of exposure to relatively pure product gas from the first tank.

The first bed 10 is connected with a reservoir or product tank 30 by way of a first check valve 32 or other unidirectional valving means. The first check valve 32 permits the primary product gas from the first bed 10 to flow into the reservoir or product tank 30 when product gas pressure in the first bed 10 exceeds the pressure of product gas in the reservoir or product tank 30. The first check valve prohibits the product gas from flowing from the reservoir or product tank 30 when the pressure in the first bed 10 is lower than the reservoir or product tank. More specific to the preferred embodiment, the check valve imposes a 1.5 psi bias such that flow is only permitted when the pressure in the first bed exceeds the pressure in the reservoir or product tank by 1.5 psi. The second bed 12 is connected with the reservoir or product tank 30 by way of a second check valve 34 or other unidirectional valving means. The second check valve 34 again provides for unidirectional flow of the primary product gas from the second bed 12 to the reservoir or product tank 30.

A pressure equalization flow path 40 extends between outlets of the first and second beds. A concentration equalization valve 42 is either open or closed to selectively permit or prevent gas flow through the flow path between the first and second beds. A control means 50 cyclically causes the cross-over valve actuating means (i.e., two solenoids) and the concentration equalization valve 42 to be operated. The control means periodically and cyclically enables a concentration equalization valve actuator which is also a solenoid.

The control means causes the cross-over valving means 20 to alternate between its first and second positions for the appropriate period during each cycle segment. A cycle segment can be either the product gas generation cycle or the purge cycle. The cycle duration is selected such that each bed is connected with the source of air for a duration which is equal to or less than the breakthrough time.

In accordance with another embodiment of the invention, the control cycle can utilize variable pressure in order to achieve a residence time within a defined range based upon a projected breakthrough time. In the preferred embodiment, the beds are 3.5 inches in diameter, 15 inches in length, and each contains 6.5 pounds of 5A zeolite.

The gas mixture is supplied up to 32 pounds of pressure to the first bed. Concurrently, the second bed (i.e., a "used" bed) is vented to atmosphere to cause purging of the nitrogen-enriched molecular sieves. Before the breakthrough time, the concentration equalization valve is opened allowing primary product-enriched gas from the first bed to flow into the evacuated second bed. Product-enriched gas is allowed to flow into the second bed to purge the sieve bed and to enrich the first product gas in the product tank. Before the primary product-enriched gas from the first bed is evacuated through the second bed, the cross-over valving means 21 is actuated to reverse its position. Actuating the cross-over valving means discontinues supplying of the gaseous mixture to the first bed and commences evacuating it and concurrently discontinues evacuating the second bed and commences supplying it with the gaseous mixture.

Subsequent to the actuation of the cross-over valving means, the concentration equalization valve 42 remains open to continue allowing a purge supply of product-enriched gas to flow into the second bed bringing the beds into equilibrium. This equalizes the concentration of gas which is supplied to the product tank since the cycling is sequenced so that the product gas proceeds the breakthrough zone to flow into the product tank. Subsequently, the concentration equalization valve closes and terminates the flow of primary-product gas between the beds. In the second segment of the cycle, the pressure in the second bed increases approaching the 32 psi gas mixture source pressure. Concurrently, the pressure in the first bed decreases approaching atmospheric pressure. Before the secondary product molecules have traversed the second bed, the concentration equalization valve 42 is opened allowing the primary product-enriched gas in the zeolite voids of the second bed to flow to the first bed. This causes the first and second beds to approach substantial pressure equilibrium. While the primary product-enriched gas is flowing to the first bed, the cross-over valving means is actuated. Actuating the cross-over valving means discontinues the evacuation of the first bed and commences supplying the gaseous mixture and concurrently discontinues supplying the gaseous mixture to the second bed and commences evacuating it. Subsequent to actuating the cross-over valving means, the concentration equalization valve is closed terminating the pressure equalizing flow of the primary product-enriched gas between the beds. The steps are cyclically repeated to provide continuing fractionating of the primary product gas from the mixture.

Figure 2:
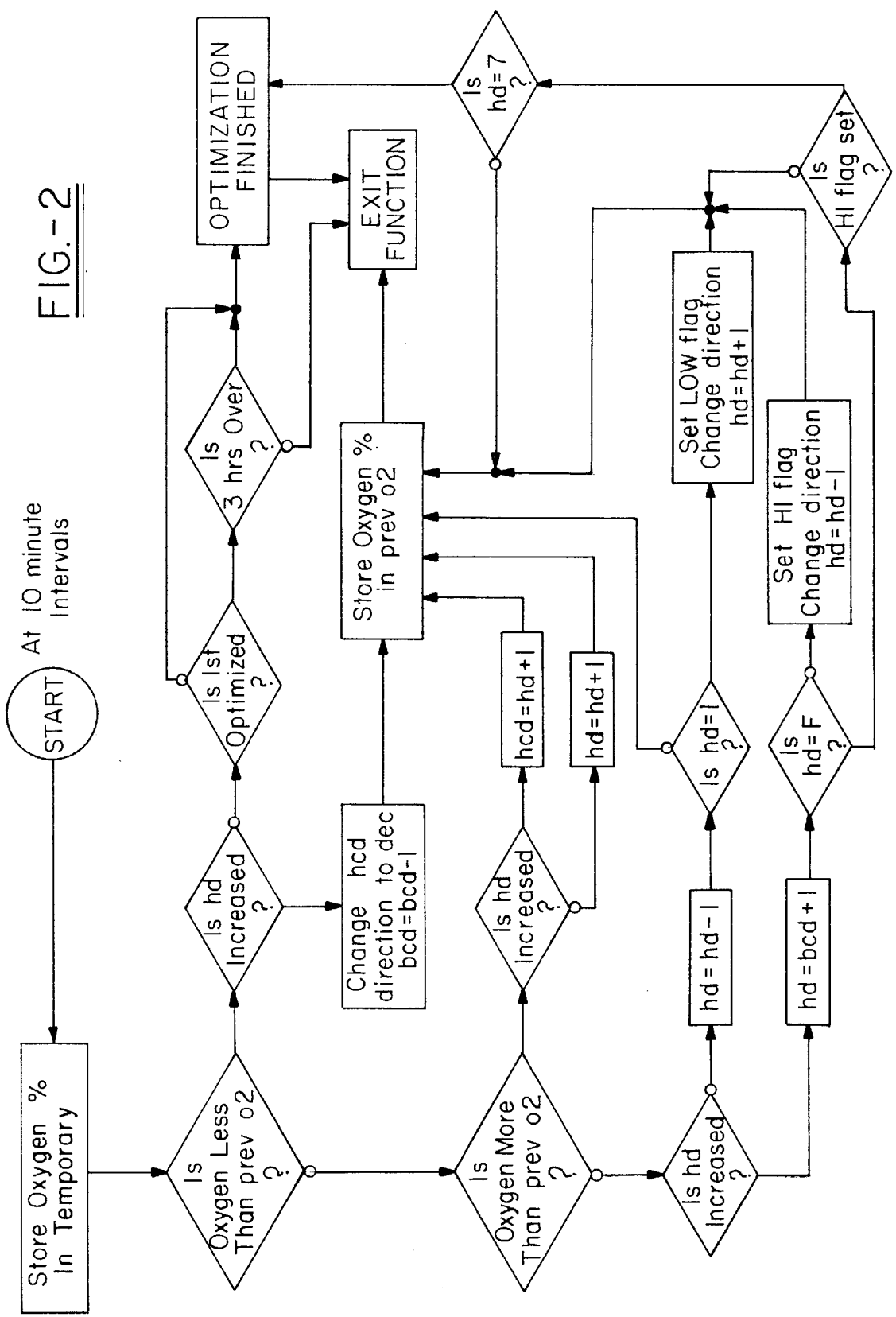
FIG. 2 is a schematic diagram showing the logic of the control circuit.

The time that the concentration equalization valve remains open (in one direction) and, consequently, the amount of primary-product gas which is allowed to flow into the bed which is being evacuated is controlled by the microprocessor to optimize (maximize) the oxygen outflow to the patient. In particular, the concentration equalization flow valve starts at an initial setting, and after a first waiting period which happens to be from about 1 minute to 1 hour, preferably from 2 minutes to 30 minutes, and more preferably from 5 to 12 minutes, the microprocessor will cause a concentration equalization flow valve adjustment means to change one time unit increment. Each time unit increment is from about 1 to about 50 milliseconds, more preferably about 10 to 30 milliseconds. After an additional incremental waiting period, i.e., a second 10-minute period, the closed-loop feedback circuit compares a voltage value from the oxygen corresponding to oxygen output to the last determined value immediately prior to the incremental time unit change. If the value increases, the microprocessor causes the concentration equalization valve adjustment means to change an additional time unit increment in the same direction (i.e., directing a longer or shorter flow of output gas into the purging bed). The microprocessor will continue this process of incremental time unit adjustment and comparison of the oxygen outflow in the same direction until the circuit senses a drop in the value at which point the circuit will direct the time unit adjustment means to step back one unit to the last optimized setting. This sequence is illustrated in FIG. 2 which is a flow chart of the control circuit.

Referring again to FIG. 1, in the preferred embodiment the reservoir or product tank 30 maintains a reservoir of oxygen at a minimum pressure of about 18 psi. The reservoir or product tank is connected with a pressure regulator 70 for controlling the pressure or flow rate of oxygen to the patient. A flow meter 72 provides a visual indication of the rate at which the patient is receiving oxygen. A humidifier 74 adds moisture to the oxygen primary product to replace the moisture removed by the beds. A breathing apparatus 76 assists in delivering the oxygen to the patient. Most medical prescriptions require that oxygen be supplied to the patient at the rate of 2 liters per minute or less. Stated differently, the system has a capacity of 1.2 pounds of oxygen per day per pound of zeolite. Eleven (11) pounds of zeolite, as in the preferred embodiment, produce 13 pounds of oxygen per day. With use, the zeolite commonly becomes contaminated with sorbents, such as water vapor, which are incompletely desorbed during evacuation. For example, it has been found that operation for 30 days with supersaturated air results in a 10 percent drop in oxygen production at 3 liters per minute.

An oxygen concentration sensor 43 is located downstream from the first check valve 32 and the second check valve 34. The sensor can advantageously be the sensor in accordance with the second embodiment of the invention or alternatively can be of the type known in the prior art. A pressure sensor 45 monitors the pressure of product gas.

The sensor monitors the oxygen content (i.e., flow rate and concentration) from the sieve beds and communicates this information by means of a control circuit to the microprocessor 50. The microprocessor 50 utilizes a closed-loop feedback circuit to operate the four-way valve (i.e., cross-over valve) solenoid 18 to switch the four-way valve setting. Specifically the microprocessor allows the four-way valve to remain in a setting such as the product evacuation setting for the first bed until the sensor 43 signals a drop in the oxygen concentration within the output line. This perceived drop corresponds to the end of the breakthrough zone within the sieve bed. FIG. 2 is a schematic illustrating how the oxygen concentration can be used to drive a switch, in this case referred to as an "HD" control device, i.e., a hexadecimal control device. The HD is used to trigger the concentration equalization valve which initiates the production cycle switch including switching of the four-way valve. Of course, a binary control switch could be substituted for the HD and likewise can trigger the concentration equalization valve switching to initiate the production cycle switch. Thus, FIG. 2 illustrates direct utilization of oxygen concentration as a control parameter for the pressure swing adsorption cycle, i.e., a drop in oxygen concentration is used to initiate switching from product flow to the product tank to use of the product in the purge of a used bed.

In response to the registered drop in oxygen concentration the concentration equalization valve is switched so as to permit a surge of higher oxygen concentration product gas into a molecular sieve bed 10 which will undergo evacuation to begin the purging of the increased nitrogen sieve bed. After a delay defined so as to provide an appropriate amount of oxygen-enriched product gas to flood the bed, the cross-over valve is switched by means of solenoid to switch the cycle segments relative to the two beds.

In accordance with a second embodiment of the invention, an oxygen sensor is provided which can be utilized in the purge control of the oxygen generation cycle but which has additional uses, such as is in an independent testing apparatus which monitors the oxygen concentration and flow rate at the patient line (i.e., posterior to the Thorpe tube).

FIGS. 3–6 illustrate this acoustic oxygen sensor which comprises a flow tube 110 that defines a smooth and substantially non-obstructed flow path 112 in its interior. In this application, "non-obstructed" means that the temperature sensor does not project into the flow path and thereby cause turbulence so as to cause false flow rate readings. A flow inlet 114 is located at a first end of the flow tube 110 and is designed to mate with a product supply conduit (not shown). A flow outlet 116 is spaced apart from the flow inlet 114 and is located at the second end of the flow tube 110. The flow outlet 116 is designed to mate with a product evacuation conduit (not shown) appropriately connected.

A temperature sensor recess 120 is provided between the inlet 114 and outlet 116 in the flow path 112. The recess 120 permits a relatively non-obtrusive fluid communication between the product flow and the temperature sensor means mounted within the recess 120. Typically the temperature sensor is a thermocouple. Advantageously, this arrangement permits adjustment of the calculations based on the sensed temperature so as to achieve accurate concentration readings without unnecessarily effecting the flow conditions which are being measured (i.e., laminar flow is optimal for a proper reading).

The flow tube 110 is closed at the first end 130 and the second end 131 by first and second stoppers 115 which each include transmitter/receiver means 134,136. These transmitter/receiver means are in substantial alignment in a direction parallel to the flow path 112 and along the longitudinal axis of the flow tube 110. Preferably the transmitter/receiver means are piezo transducers which can be activated by switching network 138 to receive or transmit pulsed waves at a given frequency respectively.

The transducers 134,136 communicate with the switching network 138 which in turn communicates with receiver and transmitters in communication with a microprocessor 150. The temperature sensor means 122 also communicates with the microprocessor 150. Visual display means such as an LCD panel display the selected variable such as the calculated oxygen concentration or flow rate.

A single-wave pulse is transmitted from one end of the cell and detected at the other end. The receiver counts the pulse and in response signals the same transmitter to send another pulse. This process is repeated for a fixed length of time, i.e., from 1 to 20 seconds, and preferably from 5 to 15 seconds. The cumulative number of pulses is communicated to microprocessor memory means. The process is then conducted in the opposite direction relative to flow (i.e., the first transmitter receives the pulsed signals and the second transmitter sends the pulsed signals). The distance is constant and the time remains fixed. The difference in the number of pulses is proportional to changes in the ambient conditions, notably a change in the oxygen concentration.

Figure 7:
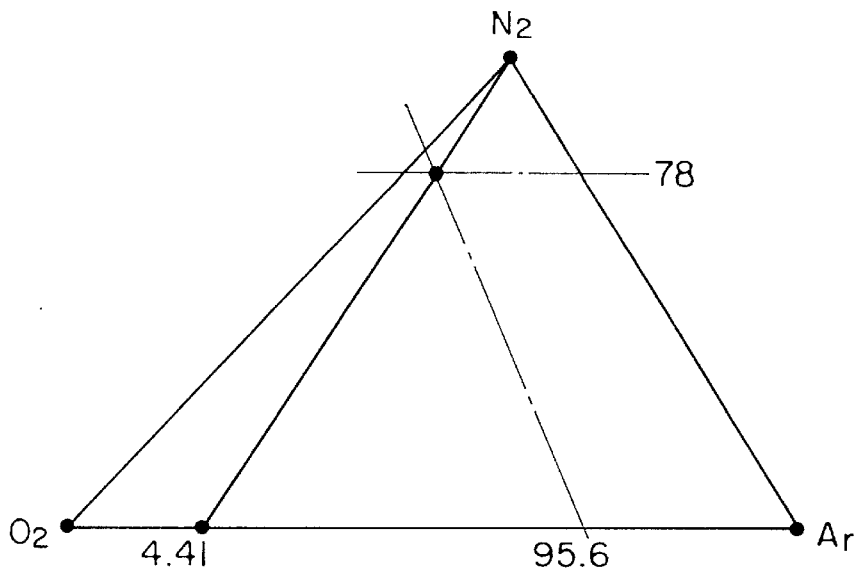
FIG. 7 is a tertiary diagram illustrating the relative concentration of the main components of air.

FIG. 7 shows a diagram of the concentration content of air for oxygen, argon, and nitrogen. This system can be thought of as a binary system in which one component is oxygen and the other component is the remaining ingredients of the air.

Figure 8:
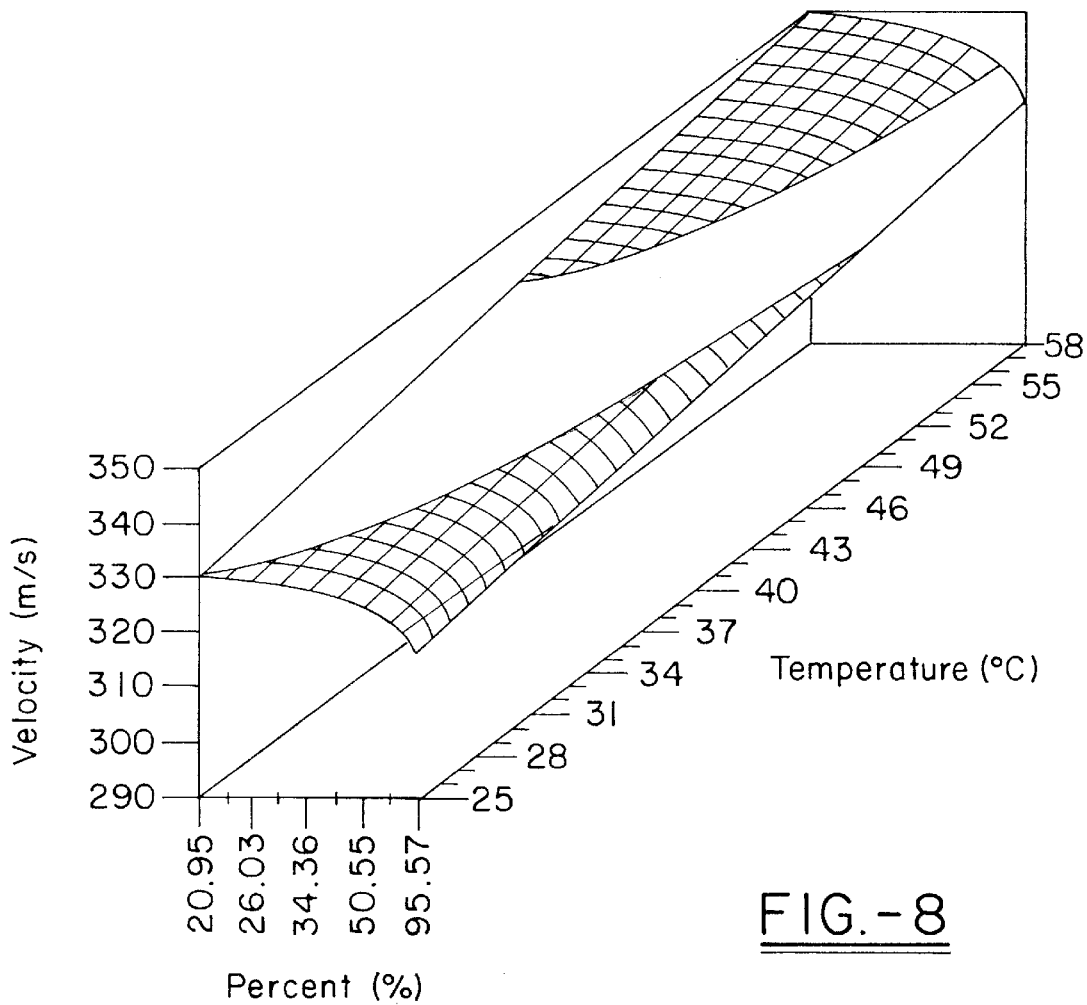
FIG. 8 is a three-dimensional graph for velocity and temperature as a function of percentage of oxygen.

FIG. 8 is a three-dimensional graph which can be used for the calculation of flow rate (i.e., velocity) as a function of oxygen percentage and temperature.

While in accordance with the patent statutes the best mode and preferred embodiment has been set forth, the scope of the invention is not limited thereto, but rather by the scope of the attached claims.

What is claimed is:

1. A method of controlling a pressure swing adsorption cycle in an oxygen concentrator having at least one fractionation bed with an inlet end in selective fluid communication with a source of pressurized air and depressurization means, said inlet end being separated by an area of fractionation medium from an output end, said output end being in fluid communication with a product tank, an oxygen sensor sensing the oxygen output from said bed, and having electronic control means capable of actuating said source of pressurized air and said depressurization means; the method comprising using said oxygen sensor to determine a value for said oxygen output of said fractionation bed; and communicating said value to said electronic control means, said electronic control means subsequently using said value to selectively initiate the fluid communication with the source of pressurized air and the depressurization means.

2. A method as set forth in claim 1 wherein said oxygen sensor is an acoustic oxygen sensor.

3. A method of controlling the pressure swing adsorption cycle in an oxygen concentrator as set forth in claim 2, wherein said oxygen concentrator further comprises at least two of said fractionation beds, and wherein each of said beds are in communication by a pressurization flow conduit with said source of pressurized air, and wherein said electronic control means allows alternate selective pressurization of said beds.

4. A method as set forth in claim 3, wherein each of said fractionation beds has an outlet end cord each of said fractionation beds is in fluid communication with the other at the output end by a concentration equalization flow path to permit a supply of oxygen-enriched air from one bed to flow to a bed being purged.

5. A method as set forth in claim 4, wherein said oxygen concentrator further includes a product tank connected to each of said beds by a first and a second output flow line, each of said beds having a unidirectional valve disposed between said bed and said product tank, and said acoustic oxygen sensor being located between the unidirectional valves of said first and said second output flow lines.

6. A method as set forth in claim 5, wherein said equalization flow path further includes a concentration equalization valve and said electronic control means actuates said concentration equalization valve to regulate a supply of oxygen-enriched air from on e fractionation bed into the other fractionation bed to initiate a purge cycle.

7. A method as set forth in claim 3, wherein each of said beds communicates selectively with said source of pressurized air and with said depressurization means and wherein a four-way valve regulates which bed is in communication with the source of pressurized air and which bed is in communication with the depressurization means.

8. A method as set forth in claim 1, wherein said depressurization means is comprised of a vent to atmosphere.

9. A method as set forth in claim 1, wherein said electronic control means comprises a microprocessor which utilizes a closed-loop feedback circuit based upon the oxygen concentration sensed by said oxygen sensor to control a fill/purge cycle.

10. An oxygen concentrator having at least two fraction beds, said beds each having an output end and inlet end connected to a pressurization flow path to an air compressor and alternatively being vented to atmosphere, said flow path being regulated by a cross-over valve, and the output end of said fractionation beds each in communication with a product tank and in communication with the other bed by a concentration equalization flow path regulated by a concentration equalization valve, said concentrator further having electronic control means in communication with said cross-over valve and said concentration equalization valve, and an acoustic oxygen sensor which determines a value for an oxygen concentration output from each of said fractionation beds, such that said electronic control means subsequently uses said value to actuate at least one of said cross-over valve and said concentration equalization valve.

11. A method as set forth in claim 10, wherein said electronic control means is remote to said oxygen concentrator.

12. An oxygen concentrator as set forth in claim 10, wherein said electronic control means utilizing a closed-loop feedback circuit based upon the oxygen concentration sensed by said acoustic oxygen sensor to control a fill/purge cycle.

13. An oxygen concentrator as set forth in claim 12, wherein said microprocessor is in telephonic communication with said oxygen concentrator.

14. An oxygen concentrator, comprising at least one fractionation bed with an inlet end in selective fluid communication with a source of pressurized air and depressurization means, said inlet end being separated by an area of fractionation medium from an output end, said output end being in selective fluid communication with a product tank, an acoustic oxygen sensor sensing the oxygen output from said bed, and electronic control means capable of actuating said source of pressurized air and said depressurization means and in communication with the acoustic oxygen sensor to determine a value for said oxygen output of said fractionation bed such that said electronic control means subsequently uses said value to selectively initiate the fluid communication with the source of pressurized air and the depressurization means.

15. An oxygen concentrator as set forth in claim 14, wherein said oxygen concentrator further comprises at least two of said fractionation beds, and wherein each of said beds are in communication by a pressurization flow conduit with said source of pressurized air, and wherein said electronic control means allows alternate selective pressurization of said beds.

16. An oxygen concentrator as set forth in claim 15, wherein each of said fractionation beds is in fluid communication with the other at the output end by a concentration equalization flow path to permit a supply of oxygen-enriched air from one bed to flow to a bed being purged.

17. An oxygen concentrator as set forth in claim 16, wherein said oxygen concentrator further includes a product tank connected to each of said beds by a first and a second output flow line, each of said beds having a unidirectional valve disposed between said bed and said product tank, and said acoustic oxygen sensor being located between the unidirectional valves of said first and said second output flow lines.

18. An oxygen concentrator as set forth in claim 17, wherein said equalization flow path further includes a concentration equalization valve and said electronic control means actuates said concentration equalization valve to regulate a supply of oxygen-enriched air from one fractionation bed into the other fractionation bed to initiate a purge cycle.

19. An oxygen concentrator as set forth in claim 15, wherein each of said beds communicates selectively with said source of pressurized air and with said depressurization means and wherein a four-way valve regulates which bed is in communication with the source of pressurized air and which bed is in communication with the depressurization means.

20. An oxygen concentrator as set forth in claim 14, wherein said depressurization means is comprised of a vent to atmosphere.

21. An oxygen concentrator as set forth in claim 14, wherein said electronic control means comprises a microprocessor which utilizes a closed-loop feedback circuit based upon the oxygen concentration sensed by said acoustic oxygen sensor to control said selective fluid communication.

22. An oxygen concentrator as set forth in claim 21, wherein said microprocessor is integral with said oxygen concentrator.

23. An oxygen concentrator as set forth in claim 21, wherein said microprocessor is remote to said oxygen concentrator.

24. An oxygen concentrator as set forth in claim 23, further comprising means to form a telephonic communication between said microprocessor and said oxygen concentrator, wherein said microprocessor is in telephonic communication with said oxygen concentrator.

25. An oxygen concentrator having at least two fractionation beds, said fractionation beds each having an output end and an inlet end connected to a pressurization flow path to an air compressor and alternatively being vented to atmosphere, said flow path being regulated by a cross-over valve, and the output end of said fractionation beds each in communication with a product tank and in communication with the other bed by a concentration equalization flow path regulated by a concentration equalization valve, said concentrator further having a microprocessor in communication with said cross-over valve and said concentration equalization valve, and an oxygen sensor which determines a value for an oxygen concentration output from each of said fractionation beds, such that said microprocessor subsequently uses said value to actuate at least one of said cross-over valve and said concentration equalization valve.

26. An oxygen concentrator as set forth in claim 25, wherein said equalization flow path further includes a concentration equalization valve and said microprocessor actuates said concentration equalization valve to regulate a supply of oxygen-enriched air from one fractionation bed into the other fractionation bed to initiate a purge cycle.

* * * * *